United States Patent
Chen et al.

(10) Patent No.: US 10,898,532 B2
(45) Date of Patent: Jan. 26, 2021

(54) METHODS FOR MANUFACTURING AND PURIFYING DRIED BURDOCK SEED EXTRACT

(71) Applicant: KANG LI BIOTECH CO., LTD., Kaohsiung (TW)

(72) Inventors: Fu-An Chen, Pingtung County (TW); Chun-Che Sung, Kaohsiung (TW); Chun Chen, Pingtung County (TW); Shih-Chiang Lee, Kaohsiung (TW)

(73) Assignee: KANG LI BIOTECH CO., LTD., Kaohsiung (TW)

( * ) Notice: Subject to any disclaimer, the term of this patent is extended or adjusted under 35 U.S.C. 154(b) by 211 days.

(21) Appl. No.: 16/174,121

(22) Filed: Oct. 29, 2018

(65) Prior Publication Data

US 2019/0134127 A1     May 9, 2019

(30) Foreign Application Priority Data

Nov. 8, 2017 (TW) .............................. 106138666 A

(51) Int. Cl.
*A61K 36/00* (2006.01)
*A61K 36/28* (2006.01)

(52) U.S. Cl.
CPC ........ *A61K 36/28* (2013.01); *A61K 2236/333* (2013.01)

(58) Field of Classification Search
None
See application file for complete search history.

(56) References Cited

U.S. PATENT DOCUMENTS 9,072,718 B2    7/2015   Okubo et al.

FOREIGN PATENT DOCUMENTS

CN           102351926 A     2/2012

*Primary Examiner* — Qiuwen Mi
(74) *Attorney, Agent, or Firm* — Innovation Capital Law Group, LLP; Vic Lin

(57) ABSTRACT

A method for manufacturing a dried burdock seed extract in order to manufacture the dried burdock seed extract rich in arctigenin is disclosed. The method includes: sequentially mixing a raw material, water and an extractant to obtain a mixture. The mixture includes 7-14 vol % of the raw material, 8-40 vol % of water and 50-84 vol % of the extractant being a 95% aqueous ethanol solution. The raw material is then extracted at a boiling condition for 20-180 minutes, followed by concentration and centrifugation to obtain the dried burdock seed extract. A method for purifying the dried burdock seed extract is also disclosed.

8 Claims, 7 Drawing Sheets

METHODS FOR MANUFACTURING AND PURIFYING DRIED BURDOCK SEED EXTRACT

CROSS REFERENCE TO RELATED APPLICATIONS

The application claims the benefit of Taiwan application serial No. 106138666, filed Nov. 8, 2017, the entire contents of which are incorporated herein by reference.

BACKGROUND OF THE INVENTION

1. Field of the Invention

The invention generally relates to a method for manufacturing a dried burdock seed extract and, more particularly, to a method for manufacturing the dried burdock seed extract rich in arcitigenin. The invention also relates to a method for purifying the dried burdock seed extract.

2. Description of the Related Art

Dried burdock seeds are mature fruits of *Arctium lappa*, general active ingredients in which includes arctiin (shown in FIG. 1a) and arcitigenin (shown in FIG. 1b). It is reported that arctiin shows effects on anti-inflammation, inhibition of lipogenesis, anti-retinopathy and anti-nephritis, where arcitigenin shows effect on anti-hypertension, protection of liver, treatment of rheumatoid arthritis, anti-fatigue, anti-arrhythmia, anti-Alzheimer's disease, protection of kidney, anti-influenza, anti-heat shock and anti-cancer.

In general, a raw sample of a dried burdock seed includes approximately 2.64-8.02% of arctiin and 0.13-1.04% of arcitigenin. Therefore, a dried burdock seed extract rich in arcitigenin cannot be obtained by extracting the raw sample of dried burdock seed. In light of this, it is necessary to provide a method for manufacturing a dried burdock seed extract and a method for purifying the dried burdock seed extract.

SUMMARY OF THE INVENTION

It is therefore an objective of the present invention to provide a method for manufacturing a dried burdock seed extract rich in arcitigenin.

It is another objective of the present invention to provide a method for purifying the dried burdock seed extract.

One embodiment of the present invention discloses a method for manufacturing the dried burdock seed extract, which includes sequentially mixing a raw material, water and an extractant to obtain a mixture including 7-14 wt % of the raw material, 8-40 wt % of water and 50-84 wt % of the extractant being a 95% aqueous ethanol solution. The raw material is then extracted at a boiling condition for 20-180 minutes to obtain a rough extract. The rough extract is concentrated under reduced pressure and centrifuged to obtain a dried burdock seed extract. Preferably, the dried burdock seed extract is obtained by centrifugation at 6,000 rpm for 15 minutes at 25° C. Accordingly, by the addition of water, arcitigenin with various bioactivity can be converted from arctiin in a raw material of a dried burdock seed by hydrolysis. Therefore, the dried burdock seed extract rich in arcitigenin can be obtained.

Another embodiment of the present invention discloses a method for purifying the dried burdock seed extract, which includes dissolving the dried burdock seed extract in a solvent being a 50% aqueous ethanol solution to obtain a saturated aqueous ethanol solution. The saturated aqueous ethanol solution is centrifuged at 6,000 rpm for 15 minutes at 25° C. to obtain an aqueous layer solution. $\frac{1}{50}$-fold resin volume of the aqueous layer solution is passed through a column filled with a resin. The column is then washed by a first elution solution ranging from 1-fold resin volume to 3-fold resin volume, followed by washing by a second elution solution ranging from 1.5-fold resin volume to 2-fold resin volume to obtain an eluate. The first elution solution is a 50-70% aqueous ethanol solution, and the second elution solution is a 95% aqueous ethanol solution. The eluate is concentrated and dried to obtain a dried burdock seed purified product. Preferably, the resin is a D101 macroporous resin. The column is washed by the first elution solution and the second elution solution in a flow rate of 5-10 mL/min. The resin is soaked in a soaking solution for 24 hours, followed by filling the resin in the column. The column is then rinsed by a rising solution ranging from 1.5-fold resin volume to 2-fold resin volume, followed by passing the aqueous layer solution through the column. The soaking solution is a 95% aqueous ethanol solution, and the rinsing solution is a 50-70% aqueous ethanol solution. More preferably, both the first elution solution and the rinsing solution are a 50% aqueous ethanol solution. Accordingly, by the use of the column, as well as the specific first and second elution solution, the dried burdock seed extract can be effectively purified. Therefore, the dried burdock seed purified product with more arcitigenin compared to the dried burdock seed extract can be obtained.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1A:
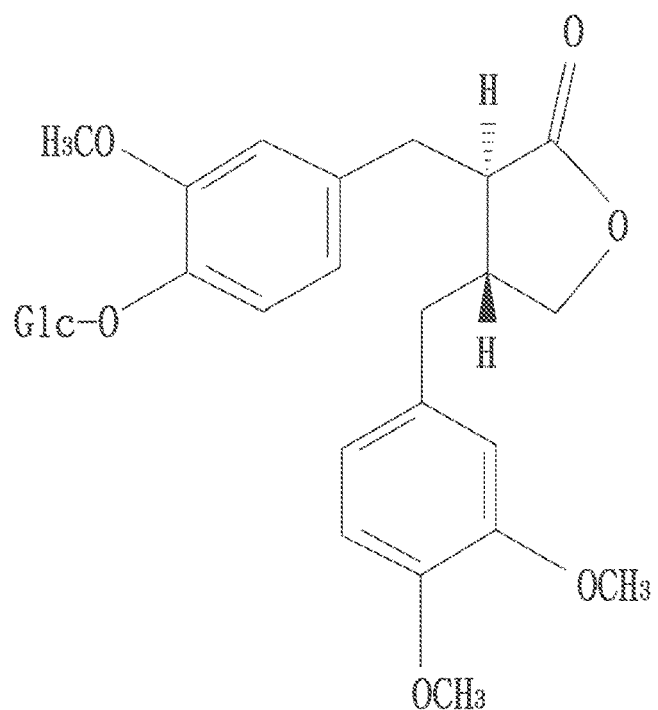
FIG. 1a depicts the chemical structure of arctiin.
Figure 1B:
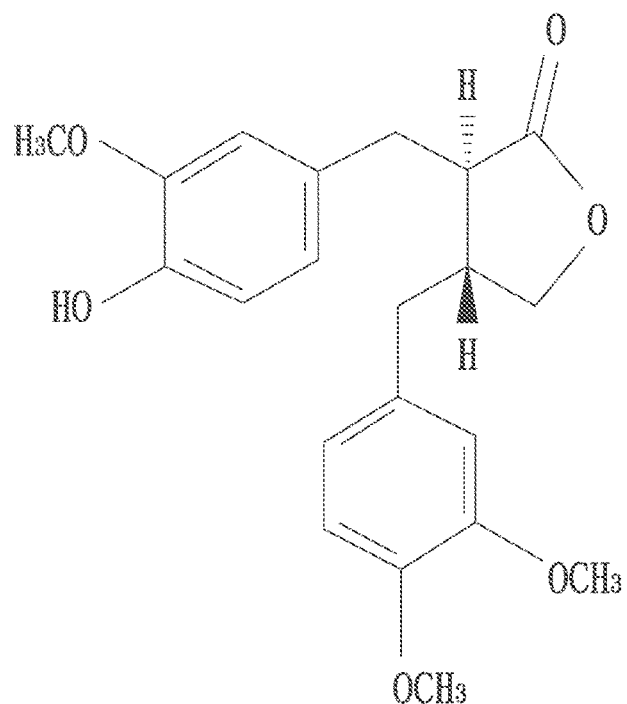
FIG. 1b depicts the chemical structure of arcitigenin.

In the various figures of the drawings, the same numerals designate the same or similar parts. Furthermore, when the term "first", "second" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

A method for manufacturing a dried burdock seed extract according to an embodiment of the present invention, in which water is added, arcitigenin with various bioactivity is converted from arctiin in a raw material of a dried burdock seed by hydrolysis.

Specifically, the raw material according to the embodiment of the present invention is a mature fruit of *Arctium lappa*. The raw material can be first milled to particles to improve the converting efficiency.

A worker can sequentially mix the raw material, water and an extractant to obtain a mixture. The mixture includes 7-14 wt % of the raw material, 8-40 wt % of water and 50-84 wt % of the extractant. As an example, the extractant can be a 95% aqueous ethanol solution with a concentration of ethanol being 95%.

Next, the raw material is extracted at a boiling condition for 20-180 minutes to obtain a rough extract. The rough extract can be concentrated under reduced pressure and centrifuged to obtain the dried burdock seed extract rich in arcitigenin. As an example, the rough extract can be centrifuged at 6,000 rpm for 15 minutes at 25° C.

According to the following method for purifying the dried burdock seed extract, a dried burdock seed purified product with more arcitigenin can be obtained from the dried burdock seed extract obtained by the method for manufacturing the dried burdock seed extract. Detail description is as following:

The dried burdock seed extract can be dissolved in a solvent (a 50% aqueous ethanol solution) to form a saturated aqueous ethanol solution, followed by centrifuging at 6,000 rpm for 15 minutes at 25° C. to form an oil layer solution (upper layer), an aqueous layer solution (lower layer) and a pellet. The aqueous layer solution can be collected as a sample for purification.

The aqueous layer solution can be passed through a column filled with the resin, arcitigenin in the aqueous layer solution can be absorbed on the resin filled in the column. Arcitigenin on the resin can then be eluted to obtain the dried burdock seed purified product rich in arcitigenin.

In this embodiment, the resin can be a D101 macroporous resin. A worker can soak the resin in a soaking solution (a 95% aqueous ethanol solution) for 24 hours, followed by being filled in the column. The resin in the column is rinsed by a rinsing solution (a 50-70% aqueous ethanol solution) ranging from 1.5-fold resin volume to 2-fold resin volume to obtain the column filled with the resin which can be used for purifying the aqueous layer solution.

The aqueous layer solution (1/50-fold resin volume) is passed through the column. A first elution solution (a 50-70% aqueous ethanol solution) ranging from 1-fold resin volume to 3-fold resin volume, and a second elution solution (a 95% aqueous ethanol solution) ranging from 1.5-fold resin volume to 2-fold resin volume are used to sequentially wash the column in a flow rate of 5-10 mL/min. to obtain an eluate. The eluate can be concentrated and dried to obtain a dried burdock seed purified product rich in arcitigenin.

To prove that the dried burdock seed extract rich in arcitigenin can be obtained according to the method for manufacturing the dried burdock seed extract, and to prove compared to the dried burdock seed extract, the dried burdock seed purified product with more arcitigenin can be obtained according to the method for purifying the dried burdock seed extract, the following trials are carried out.

Trial (A).

In trial (A), the raw material is sequentially mixed with water and the extractant (95% aqueous ethanol solution), and is extracted at boiling condition to obtain the dried burdock seed extract of group A1. Moreover, the raw material is mixed with the extractant, followed by extracting to obtain the dried burdock seed extract of group A0.

Figure 2A:
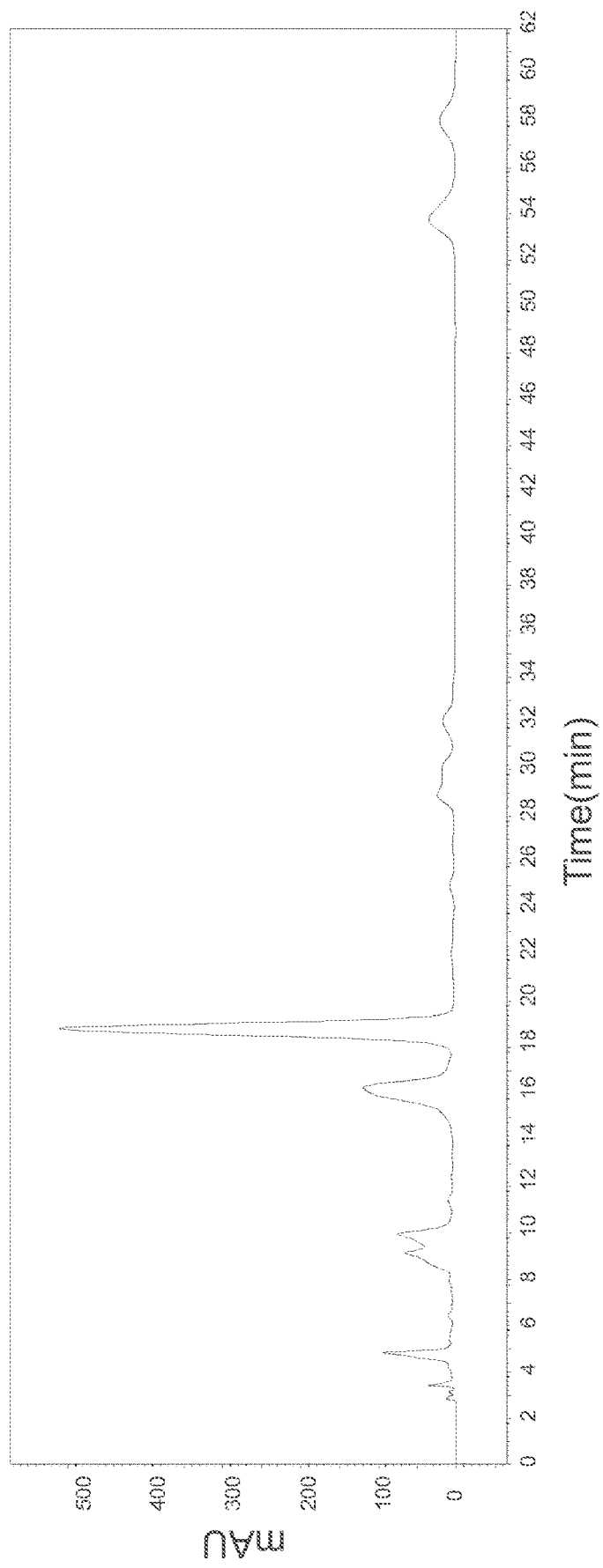
FIG. 2a depicts a HPLC chromatogram of the dried burdock seed extract of group A0.
Figure 2B:
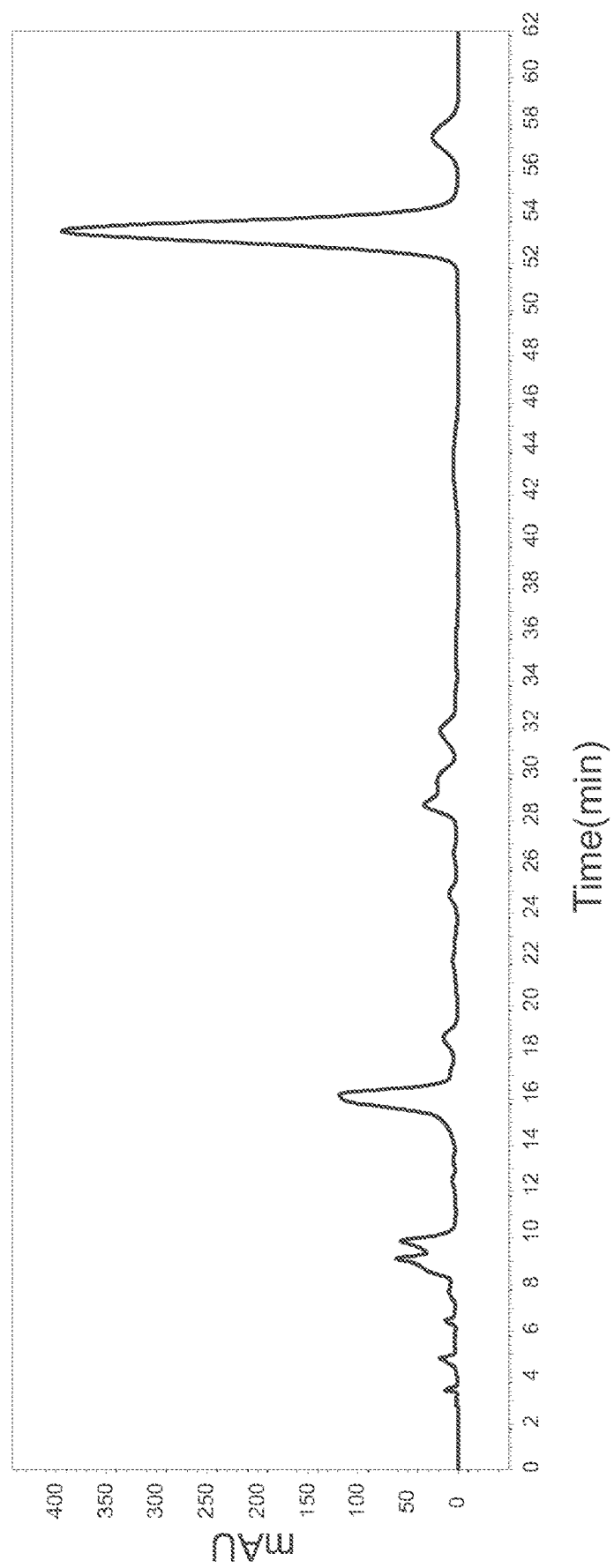
FIG. 2b depicts a HPLC chromatogram of the dried burdock seed extract of group A1.

The dried burdock seed extracts of groups A0-A1 are analyzed by HPLC under the parameters: Cosmosil 5C18-MS-II (i.d. 4.6×250 mm, 5 μm), scanning at 200-900 nm, analyzing time being 62 minutes, flow rate being 0.8 mL/minute, injection of 10 μL, mobile phase being methanol-32 mM HCl solution (V/W of 38:62), for isocratic elution. The HPLC chromatograms are shown in FIGS. 2a and 2b, respectively. Moreover, as shown in TABLE 1, arctiin level and arcitigenin level are calculated using the external standard method according to FIGS. 2a and 2b.

TABLE 1

| Groups | active ingredient | |
|---|---|---|
| A0 | arctiin (mg/g) | 182.77 ± 6.6 |
| | arcitigenin (mg/g) | 14.39 ± 2.94 |
| | arcitigenin/arctiin | 0.08 |
| A1 | arctiin (mg/g) | 67.32 ± 14.13 |
| | arcitigenin (mg/g) | 360.30 ± 44.91 |
| | arcitigenin/arctiin | 5.57 |

Referring to TABLE 1, compared to arcitigenin/arctiin ratio of the dried burdock seed extract of group A0, the dried burdock seed extract of group A1 has a higher arcitigenin/arctiin ratio, indicating that the method for manufacturing the dried burdock seed extract help convert arctiin in the raw material to arcitigenin with various bioactivity by hydrolysis, forming the dried burdock seed extract rich in arcitigenin.

Trial (B).

Figure 3A:
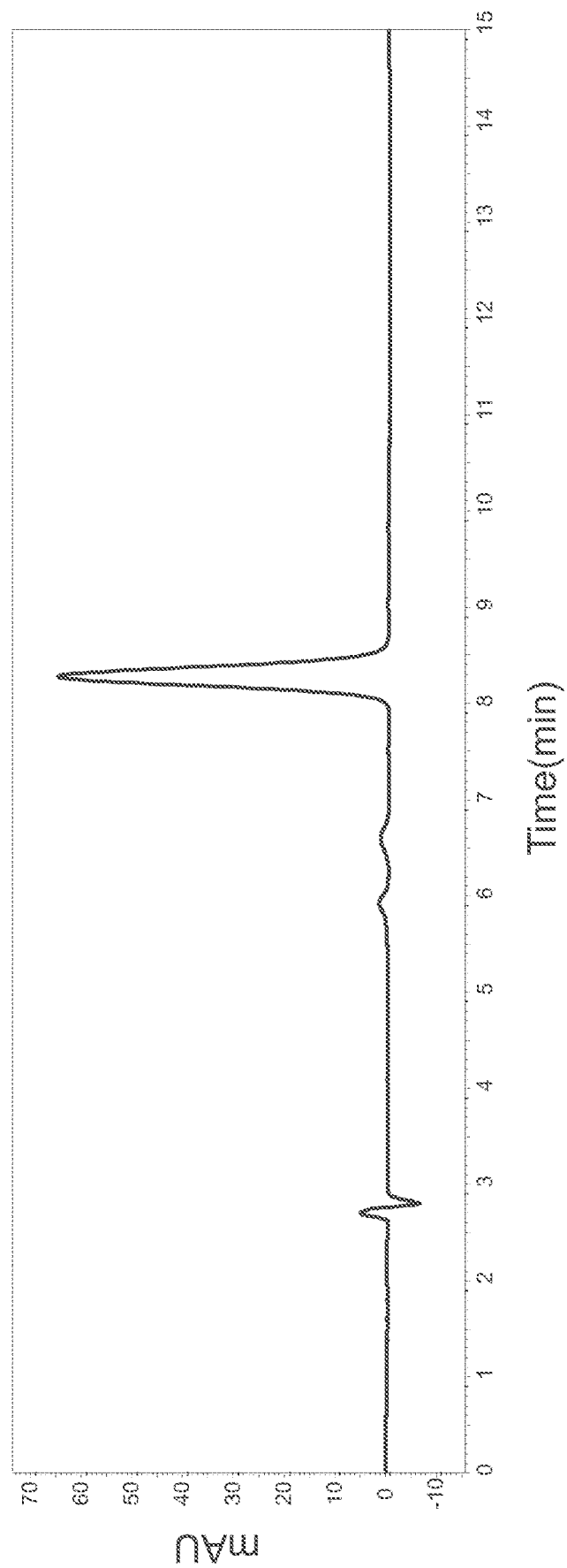
FIG. 3a depicts a HPLC chromatogram of the sample for purification of group B1.
Figure 3B:
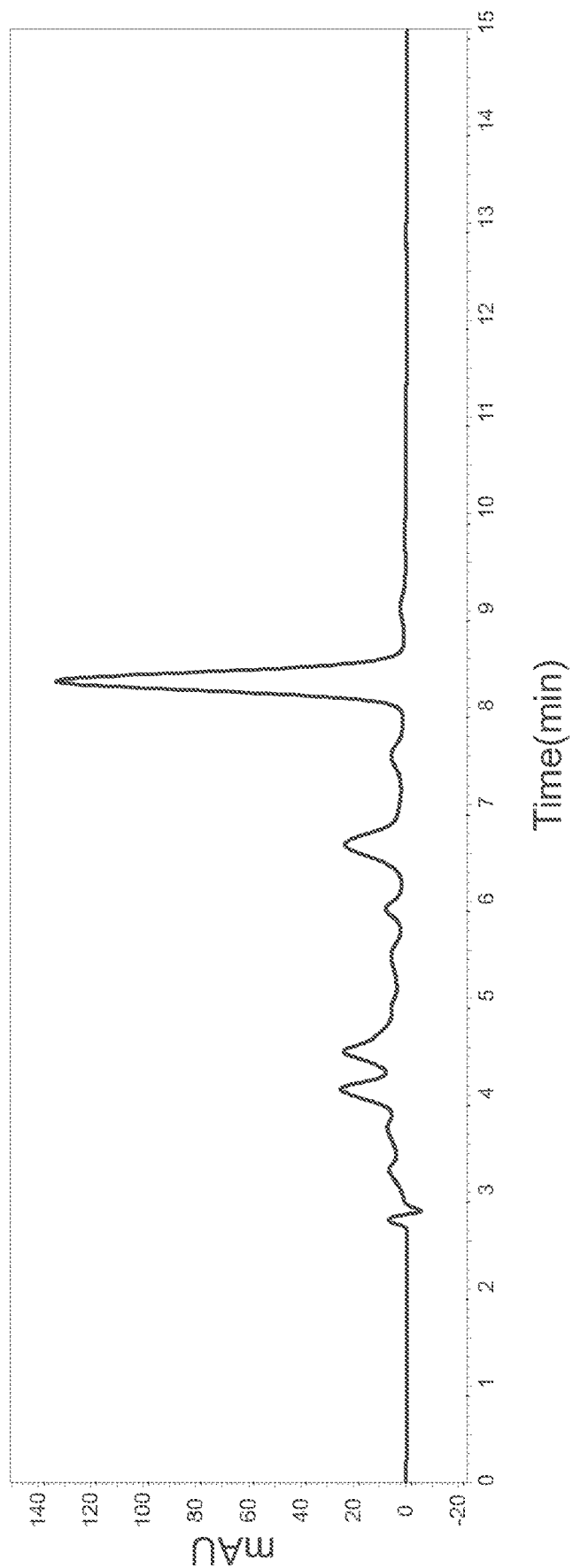
FIG. 3b depicts a HPLC chromatogram of the sample for purification of group B2.
Figure 3C:
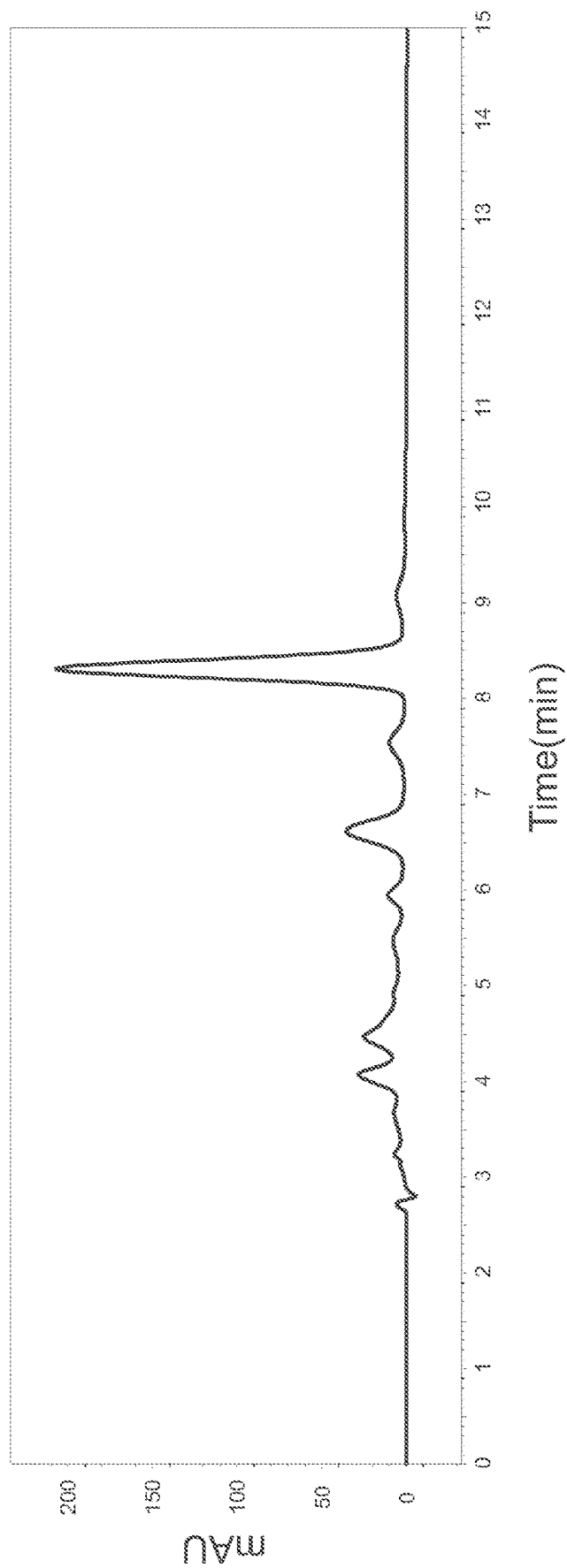
FIG. 3c depicts a HPLC chromatogram of the sample for purification of group B3.

In trial (B), the dried burdock seed extract of group A1 is dissolved in the solvent (50% aqueous ethanol solution) to form the saturated aqueous ethanol solution, followed by centrifugation to obtain the oil layer solution, the aqueous layer solution and the pellet. The oil layer solution, the aqueous layer solution and the pellet used as the sample for purification of groups B1, B2 and B3, respectively are diluted, followed by HPLC analysis under the parameters: Cosmosil 5C18-MS-II (i.d. 4.6×250 mm, 5 μm), scanning at 200-900 nm, analyzing time being 62 minutes, flow rate being 0.8 mL/minute, injection of 10 μL, mobile phase being methanol-32 mM HCl solution (V/W of 38:62), for isocratic elution. The HPLC chromatograms are shown in FIGS. 3a, 3b and 3c, respectively. Moreover, as shown in TABLE 2, arctiin level and arcitigenin level are calculated using the external standard method according to FIGS. 3a, 3b and 3c.

TABLE 2

| Groups | active ingredient | |
|---|---|---|
| B1 [1] | arctiin (mg/g) | 0.13 |
| | arcitigenin (mg/g) | 20.93 |
| | arcitigenin/arctiin | 161 |
| B2 [1] | arctiin (mg/g) | 13.37 |
| | arcitigenin (mg/g) | 41.54 |
| | arcitigenin/arctiin | 3.11 |
| B3 [1] | arctiin (mg/g) | 1.51 |
| | arcitigenin (mg/g) | 6.33 |
| | arcitigenin/arctiin | 4.19 |

[1] The oil layer solution and the aqueous layer solution are diluted 200 fold for HPLC analysis, while the pellet is diluted 20 fold for HPLC analysis.

Referring to TABLE 2, compared to arcitigenin/arctiin ratio of the sample for purification of group B3, the samples for purification of groups B1 and B2 have higher arcitigenin/arctiin ratio. However, the sample for purification of group B1 is an oil layer which is not suitable for passing through the column. Therefore, the sample for purification of group B2 is used for the purification process in the following trial.

Trial (C).

Figure 4:
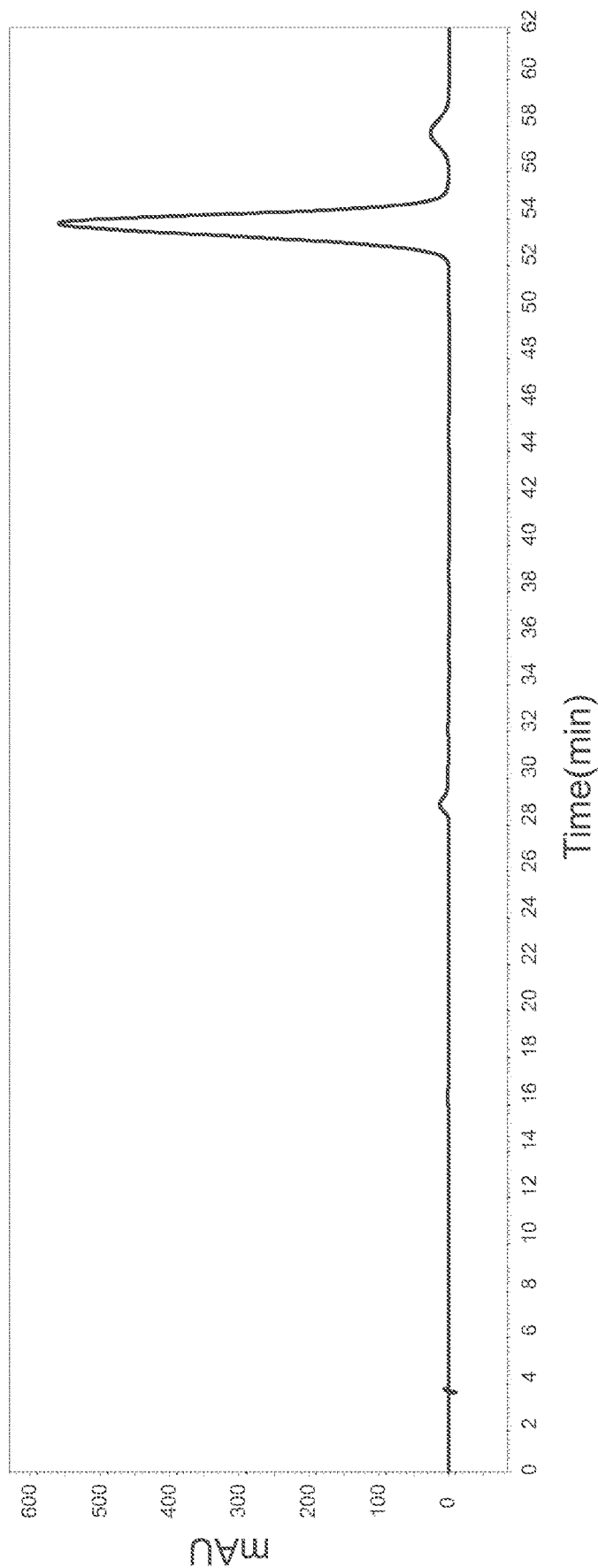
FIG. 4 depicts a HPLC chromatogram of the dried burdock seed purified product of group C.

In trial (C), the sample for purification of group B2 is passed through the column filled with the resin, followed by sequentially washing by the first elution solution (50-70% aqueous ethanol solution) and the second elution solution (95% aqueous ethanol solution) to obtain the eluate for HPLC analysis under the parameters: Cosmosil 5C18-MS-II (i.d. 4.6×250 mm, 5 μm), scanning at 200-900 nm, analyzing time being 62 minutes, flow rate being 0.8 mL/minute, injection of 10 μL, mobile phase being methanol-32 mM HCl solution (V/W of 38:62), for isocratic elution. The HPLC chromatograms are shown in FIG. 4. Moreover, using the external standard method according to FIG. 4, arctiin level is 27.38±17.68 mg/g, arcitigenin level is 580.95±29.03 mg/g, and arcitigenin/arctiin ratio is 21.21, which is significantly increased compared to the dried burdock seed extract of group A1. That is, by the method for purifying the dried burdock seed extract, the dried burdock seed purified product rich in arcitigenin can be obtained.

Accordingly, by the addition of water, arcitigenin with various bioactivity can be converted from arctiin in a raw material of a dried burdock seed by hydrolysis. Therefore, the dried burdock seed extract rich in arcitigenin can be obtained.

Moreover, by the use of the column, as well as the specific first and second elution solution, the dried burdock seed extract can be effectively purified. Therefore, the dried burdock seed purified product with more arcitigenin compared to the dried burdock seed extract can be obtained.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for manufacturing a dried burdock seed extract, comprising:
    sequentially mixing a raw material of a dried burdock seed, water and an extractant to obtain a mixture including 7-14 wt % of the raw material, 8-40 wt % of water and 50-84 wt % of the extractant being a 95% aqueous ethanol solution;
    extracting the raw material by the extractant at a boiling condition for 20-180 minutes to obtain a rough extract; and
    concentrating under reduced pressure and centrifuging the rough extract to obtain the dried burdock seed extract.

2. The method for manufacturing the dried burdock seed extract as claimed in claim 1, wherein the rough extract is centrifuged at 6,000 rpm for 15 minutes at 25° C. to obtain the dried burdock seed extract.

3. A method for purifying a dried burdock seed extract, comprising:
    obtaining the dried burdock seed extract by a method for manufacturing the dried burdock seed extract as claimed in claim 1;
    solving the dried burdock seed extract in a solvent of a 50% aqueous ethanol solution to obtain a saturated aqueous ethanol solution;
    centrifuging the saturated aqueous ethanol solution at 6,000 rpm for 15 minutes at 25° C. to obtain an aqueous layer solution;
    passing 1/50-fold resin volume of the aqueous layer solution through a column filled with the resin;
    washing the column by a first elution solution ranging from 1-fold resin volume to 3-fold resin volume, followed by washing the column by a second elution solution ranging from 1.5-fold resin volume to 2-fold resin volume to obtain an eluate; and
    concentration and drying the eluate to obtain a dried burdock seed purified product;
    wherein the first elution solution is a 50-70% aqueous ethanol solution, and the second elution solution is a 95% aqueous ethanol solution.

4. The method for purifying the dried burdock seed extract as claimed in claim 3, wherein the resin is a D101 macroporous resin.

5. The method for purifying the dried burdock seed extract as claimed in claim 3, wherein the column is washed by the first elution solution and the second elution solution in a flow rate of 5-10 mL/min.

6. The method for purifying the dried burdock seed extract as claimed in claim 3, further comprising:
    soaking the resin in a soaking solution for 24 hours, followed by filling the resin in the column; and
    rinsing the column filled with the resin by a rinsing solution ranging from 1.5-fold resin volume to 2-fold resin volume, followed by passing the aqueous layer solution through the column filled with the resin;
    wherein the soaking solution is a 95% aqueous ethanol solution, and the rinsing solution is a 50-70% aqueous ethanol solution.

7. The method for purifying the dried burdock seed extract as claimed in claim 3, wherein the first elution solution is a 50% aqueous ethanol solution.

8. The method for purifying the dried burdock seed extract as claimed in claim 6, wherein the rinsing solution is a 50% aqueous ethanol solution.

* * * * *